United States Patent [19]

Taylor et al.

[11] Patent Number: 5,248,775
[45] Date of Patent: Sep. 28, 1993

[54] PYRROLO(2,3-D)PYRIMIDINES

[75] Inventors: Edward C. Taylor, Princeton, N.J.; Dietmar G. Kuhnt, Leverkusen, Fed. Rep. of Germany; Chuan Shih, Carmel; Gerald B. Grindey, Indianapolis, both of Ind.

[73] Assignee: The Trustees of Princeton University, Princeton, N.J.

[21] Appl. No.: 830,111

[22] Filed: Jan. 31, 1992

Related U.S. Application Data

[60] Continuation-in-part of Ser. No. 674,541, Mar. 22, 1991, and Ser. No. 686,119, Apr. 15, 1991, abandoned, which is a division of Ser. No. 528,155, May 24, 1990, Pat. No. 5,028,608, which is a continuation-in-part of Ser. No. 448,742, Dec. 11, 1989, abandoned, said Ser. No. 674,541, is a continuation-in-part of Ser. No. 448,742, Dec. 11, 1989.

[51] Int. Cl.$^5$ .......................................... C07D 487/04
[52] U.S. Cl. .................................................... 544/280
[58] Field of Search ......................................... 544/280

[56] References Cited

U.S. PATENT DOCUMENTS 5,106,974  4/1992  Akimoto et al. .................... 544/280

FOREIGN PATENT DOCUMENTS 418924  3/1991  European Pat. Off. .
438261  7/1991  European Pat. Off. ............ 544/280

OTHER PUBLICATIONS

Akimoto et al, Chemical Abstracts, vol. 115, No. 71633 (1991) (Abstract for EP 418924, Mar. 27, 1991).

Primary Examiner—Emily Bernhardt
Attorney, Agent, or Firm—Mathews, Woodbridge & Collins

[57] ABSTRACT

3-Ethynylpyrrolo[2,3-d]pyrimidines are chemical intermediates for antineoplastic N-(acyl)glutamic acid derivatives. A typical embodiment is 3-ethynyl-4-hydroxy-6-pivaloylaminopyrrolo[2,3-d]pyrimidine.

8 Claims, No Drawings

PYRROLO(2,3-D)PYRIMIDINES

CROSS-REFERENCE TO RELATED APPLICATIONS

This is a continuation-in-part of Ser. No. 07/674,541 pending filed Mar. 22, 1991 and Ser. No. 07/686,119 filed Apr. 15, 1991, now abandoned Ser. No. 07/686,119 is a divisional of Ser. No. 07/528,155 filed May 24, 1990, now U.S. Pat. No. 5,028,608. Each of Ser. Nos. 07/528,155 and 07/674,541 pending in turn is a continuation-in-part of Ser. No. 07/448,742, filed Dec. 11, 1989, now abandoned.

DETAILED DESCRIPTION

The disclosures of Ser. Nos. 07/528,155 and 07/674,541 are incorporated herein by reference. These and the related applications enumerated above disclose antineoplastic glutamic acid derivatives represented by the formula:

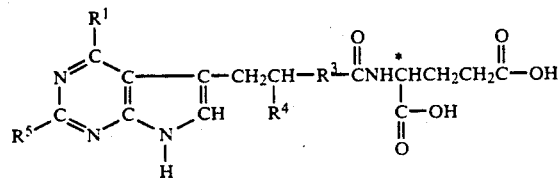

In Formula I, $R^1$ is —OH or —$NH_2$; $R^3$ is phenylene, thienediyl, furanediyl, cyclohexanediyl, or alkanediyl; $R^4$ is hydrogen, methyl, or hydroxymethyl; and $R^5$ is hydrogen, methyl, or amino. The configuration about the carbon atom designated * is S.

The present invention pertains to chemical intermediates useful in the preparation of glutamic acid derivatives of Formula I. In particular, these intermediates are unsaturated compounds represented by the formula:

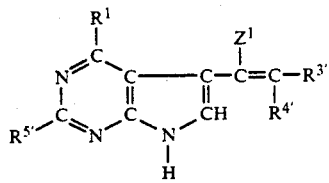

in which
$R^1$ is —OH or —$NH_2$;
$R^{3'}$ is hydrogen, a trisubstituted silyl group, or —$R^3$—$R^7$;
$R^3$ is phenylene, thienediyl, furanediyl, cyclohexanediyl, or alkanediyl;
$R^7$ is —$COOR^{2'}$, or —CONHČH($COOR^{2'}$)$CH_2CH_2COOR^{2'}$;
$R^{2'}$ is hydrogen or a carboxy protecting group;
$R^{4'}$, when taken independently of $Z^1$, is hydrogen, methyl, hydroxymethyl, or hydroxymethyl substituted with a hydroxy protecting group;
$R^5$ is hydrogen, methyl, amino, or amino carrying a protecting group; and
$Z^1$ is hydrogen, or $Z^1$ taken together with $R^{4'}$ is a carbon-carbon bond.

The pyrrolo[2,3-d]pyrimidine heterocyclic ring system of both the intermediates and final compounds is numbered herein as follows:

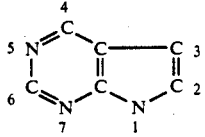

It will be appreciated that the pyrrolo[2,3d]pyrimidines depicted herein are the tautomeric equivalents of the corresponding 5-H-4-oxo or 5-H-4-imino structures. Unless otherwise indicated, for simplicity's sake the compounds are depicted herein and named using the 4-hydroxy and 4-amino convention, it being understood the 5-H-4-oxo and 5-H-4-imino structures are fully equivalent.

In the simplest case, $R^{3'}$ can be hydrogen or a protected derivative thereof such as a trisubstituted silyl group. Alternatively, $R^{3'}$ can be —$R^3$—$R^7$ in which $R^3$ is a divalent group having at least two carbon atoms between the carbon atoms carrying the free valence bonds. $R^3$ for example can be a 1,4-phenylene or 1,3-phenylene ring which is unsubstituted or optionally substituted with chloro, fluoro, methyl, methoxy, or trifluoromethyl. Alternatively, $R^3$ can be a thienediyl or furanediyl group, that is, a thiophene or furane ring from which two hydrogen atoms have been removed from two ring carbon atoms, as for example the thiene-2,5-diyl, thiene-3,5-diyl, thiene-2,4-diyl, and thiene-3,4-diyl ring systems, and the furane-2,5-diyl, furane-3,5-diyl, furane-2,4-diyl, and furane-3,4-diyl ring systems, which ring systems can be unsubstituted or substituted with chloro, fluoro, methyl, methoxy, or trifluoromethyl. It will be appreciated that whereas in the abstract the thiene-3,5-diyl system is the equivalent of the thiene-2,4-diyl system, the two terms are utilized herein to denote the two isomeric forms resulting from the orientation of the thiophene ring within the remainder of the molecule: e.g. the structure in which the depicted carboxy group adjacent to $R^3$ is in the 2-position of the thiophene ring and that in which the depicted carboxy group adjacent to $R^3$ is in the 3-position of the thiophene ring. The same conventions apply to the furane ring. $R^3$ also can be a cyclohexanediyl group, namely a divalent cycloalkane group of 6 carbon atoms such as cyclohexane-1,3-diyl and cyclohexane-1,4-diyl. Finally, $R^3$ can be a alkanediyl, namely a straight or branched divalent aliphatic group of from 2 to 4 carbon atoms such as ethano, trimethylene, tetramethylene, propane-1,2-diyl, propane-2,3-diyl, butane-2,3-diyl, butane-1,3-diyl, and butane-2,4-diyl. It again will be appreciated that whereas in the abstract propane-1,2-diyl is the equivalent of propane-2,3-diyl, and butane-1,3-diyl the equivalent of butane-2,4-diyl, the two terms are utilized herein to denote the two isomeric forms resulting from the orientation of an unsymmetrical alkanediyl chain with respect to the remainder of the molecule.

The protecting groups designated by $R^{2'}$, $R^{4'}$ and $R^{5'}$ and utilized herein denote groups which generally are not found in the final therapeutic compounds but which are intentionally introduced at some stage of the synthesis in order to protect groups which otherwise might react in the course of chemical manipulations, thereafter being removed at a later stage of the synthesis. Since compounds bearing such protecting groups thus are of importance primarily as chemical intermediates, the precise structure of the protecting group is not critical. Numerous reactions for the formation and removal of such protecting groups are described in a number of standard works including, for example, "Protective Groups in Organic Chemistry", Plenum Press, London and New York, 1973; Greene, Th. W. "Protective Groups in Organic Synthesis", Wiley, New York, 1981; "The Peptides", Vol. I, Schröder and Lubke, Academic Press, London and New York, 1965; "Methoden der organischen Chemie", Houben-Weyl, 4th Edition, Vol.15/I, Georg Thieme Verlag, Stuttgart 1974, the disclosures of which are incorporated herein by reference.

A carboxy group such as $R^{2'}$ can be protected as an ester group which is selectively removable under sufficiently mild conditions not to disrupt the desired structure of the molecule, especially a lower alkyl ester of 1 to 12 carbon atoms such as methyl or ethyl and particularly one which is branched at the 1-position such as t-butyl; and such lower alkyl ester substituted in the 1- or 2-position with (i) lower alkoxy, such as for example, methoxymethyl, 1-methoxyethyl, and ethoxymethyl, (ii) lower alkylthio, such as for example methylthiomethyl and 1-ethylthioethyl; (iii) halogen, such as 2,2,2-trichloroethyl, 2-bromoethyl, and 2-iodoethoxycarbonyl; (iv) one or two phenyl groups each of which can be unsubstituted or mono-, di- or tri-substituted with, for example lower alkyl such as tert-butyl, lower alkoxy such as methoxy, hydroxy, halo such as chloro, and nitro, such as for example, benzyl, 4-nitrobenzyl, diphenylmethyl, di-(4-methoxyphenyl)methyl; or (v) aroyl, such as phenacyl. A carboxy group also can be protected in the form of an organic silyl group such as trimethylsilylethyl or tri-lower alkylsilyl, as for example trimethylsilyloxycarbonyl.

A hydroxy group, as in the case of $R^{4'}$ being hydroxymethyl, can be protected through the formation of acetals and ketals, as for example through formation of the tetrahydropyr-2-yloxy (THP) derivative.

An amino group, as in the case of $R^{5'}$, can be protected as an amide utilizing an acyl group which is selectively removable under mild conditions, especially formyl, a lower alkanoyl group which is branched α to the carbonyl group, particularly tertiary alkanoyl such as pivaloyl, or a lower alkanoyl group which is substituted in the position α to the carbonyl group, as for example trifluoroacetyl.

When $Z^1$ taken together with $R^{4'}$ is a carbon-carbon bond, a triple bond is present between the two carbon atoms to which $Z^1$ and $R^{4'}$ are bound. When on the other hand $Z^1$ and $R^{4'}$ are taken separately, as when each is hydrogen, a double bond is present between the two carbon atoms to which $Z^1$ and $R^{4'}$ are bound.

As described in greater detail in the foregoing patents and applications, the compounds of Formula I can be prepared through hydrogenation of a compound of Formula II, utilizing noble metal and noble metal oxide catalysts such as palladium or platinum oxide, rhodium oxide. Protecting groups encompassed by $R^{2'}$, $R^{4'}$ and/or $R^{5'}$ then can be removed through acidic or basic hydrolysis, as for example with hydrogen chloride to cleave an $R^{4'}$ protecting group or with sodium hydroxide to cleave $R^{2'}$ or $R^{5'}$ protecting groups, thereby yielding the compounds of Formula I. Methods of removing the various protective groups are described in the standard references noted above and incorporated herein by reference.

Compounds of Formula II are prepared through procedures analogous to those described in U.S. Pat. No. 4,818,819, the disclosure of which is incorporated herein by reference, utilizing however halogenated pyrrolo[2,3-d]pyrimidines in place of pyrido[2,3-d]pyrimidines. Thus a pyrrolo[2,3-d]pyrimidine of the formula:

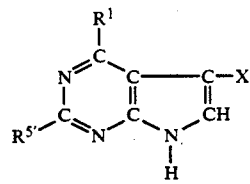

III in which X is bromo or iodo and $R^{5'}$ is as herein defined, is allowed to react with an unsaturated compound of the formula:

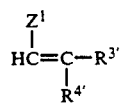

V in which $Z^1$, $R^{3'}$, and $R^{4'}$ are as herein defined, in the presence of a palladium/trisubstituted phosphine catalyst of the type described in U.S. Pat. No. 4,818,819.

A compound of Formula II in which $R^{3'}$ is hydrogen also can be converted to compounds of Formula II in which $R^{3'}$ is other than hydrogen, again utilizing the procedures described in U.S. Pat. No. 4,818,819. Thus a compound of the formula:

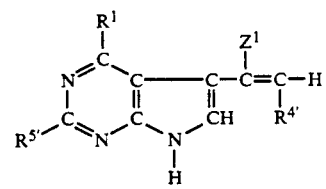

IIA in which $Z^1$, $R^{4'}$, and $R^{5'}$ are as herein defined, is allowed to react with a compound of the formula:

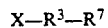

IV in which X, $R^3$, and $R^7$ are as herein defined, in the presence of a palladium/trisubstituted phosphine catalyst of the type described in U.S. Pat. No. 4,818,819 to yield compounds of Formula II in which $R^{3'}$ is —$R^3$—$R^7$.

The pyrrolo[2,3-d]pyrimidine starting materials of Formula III above can be obtained by treating a compound of the formula:

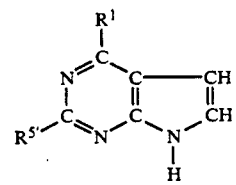

V in which $R^{5'}$ is as herein defined with N-iodosuccinimide or N-bromosuccinimide to yield the corresponding 2,3-diiodopyrrolo[2,3-d]pyrimdine or 2,3-dibromopyrrolo[2,3-d]pyrimidine which then is treated with zinc and acetic acid to remove selectively the iodine or bromine atom in the 2-position, yielding the corresponding 3-iodopyrrolo[2,3-d]pyrimidine or 3-bromopyrrolo[2,3-d]pyrimidine of Formula III.

A compound of Formula II in which $R^1$ is —OH can be converted to the corresponding compound of Formula II in which $R^1$ is —NH$_2$ through the initial use of 1,2,4-triazole and (4-chlorophenyl)dichlorophosphate, followed by treatment of the intermediate product with concentrated ammonia.

The following examples will serve to further illustrate the invention. In the NMR data, "s" denotes singlet, "d" denotes doublet, "t" denotes triplet, "q" denotes quartet, "m" denotes multiplet, and "br" denotes a broad peak.

EXAMPLE 1

3-Iodo-4-hydroxy-6-pivaloylamino-pyrrolo[2,3-dipyrimidine

A mixture of 3.0 g (0.02 mole) of 4-hydroxy-6-aminopyrrolo[2,3-d]pyrimidine and 8.4 g (0.07 mol) of pivaloyl chloride in 40 mL of pyridine is stirred for 30 minutes at from 80° to 90° C., the mixture then evaporated to dryness, and the residue dissolved in 30 mL of methanol. Addition of 10% aqueous ammonia yields 4.2 g (89%) of 4-hydroxy-6-pivaloylaminopyrrolo[2,3-d]pyrimidine which can be further purified by chromatography through silica gel, eluting with 8% methanol in methylene p chloride. mp 295° C. $^1$NMR (d$_6$-DMSO) δ1.20(s, 9H), 6.37(d, J=3.4Hz, 1H), 6.92(d, J=3.4Hz, 1H), 10.78 (s, 1H), 11.56 (s, 1H), 11.82 (s, 1H). Anal. Calc. for $C_{11}H_{14}N_4O_2C$, 56.40; H, 6.02; N, 23.92. Found: C, 56.16; H, 6.01; N, 23.67.

To a mixture of 4.7 g (20 mmol) of 4-hydroxy-6-pivaloylaminopyrrolo[2,3-d]pyrimidine in 200 mL of dimethylformamide are added 9.9 g (44 mmol) of N-iodosuccinamide. The mixture is stirred at ambient temperature in the dark for 18 hours. Most of the dimethylformamide is removed by evaporation and the residual slurry poured into 300 mL of water. The resulting solid is collected by filtration and dried under vacuum over phosphorus pentoxide to yield 2,3-diiodo-4-hydroxy-6-pivaloylaminopyrrolo[2,3-d]pyrimidine which can be purified further by chromatography over silica eluting with 2.5% methanol in methylene chloride. mp >290° C. $^1$NMR (d$_6$-DMSO) δ1.18(s, 9H), 10.85 (s, 1H), 11.85 (s, 1H), 12.42 (s, 1H). Anal. Calc. for $C_{11}H_{12}N_4O_2I_2$: C, 27.18; H 2.49; N, 11.53; I, 52.22. Found: C, 27.51; H, 2.51; N, 11.27;I, 52.02.

In a similar fashion but starting with 4-hydroxy-6-methylpyrrolo[2,3-d]pyrimidine and 4-hydroxypyrrolo[2,3-d]pyrimidine (7-deazahypoxanthine) there are respectively obtained 2,3-diiodo-4-hydroxy-6-methylpyrrolo[2,3-d]pyrimidine and 2,3-diiodo-4-hydroxypyrrolo[2,3-d]pyrimidine, mp >205° C. (compound loses iodine). $^1$NMR (d$_6$-DMSO) δ7.79 (s, 1H), 11.93 (s, 1H), 12.74 (s, 1H).

To a mixture of 4.86 g of 2,3-diiodo-4-hydroxy-6-pivaloylaminopyrrolo[2,3-d]pyrimidine in 100 mL of glacial acetic acid and 25 mL of water are added 1.3 g (20 mmol) of zinc powder. The mixture is stirred at ambient temperature for 18 hours, diluted with 500 mL of water, and cooled. The solid is collected through filtration and dried under vacuum over phosphorus pentoxide to yield 3-iodo-4-hydroxy-6-pivaloylaminopyrrolo[2,3-d]pyrimidine which can be purified further by chromatography over silica eluting with 2.5% methanol in methylene chloride.
mp >240° C.

$^1$NMR (d$_6$-DMDO) δ1.20(s, 9H), 7.12 (d, J=1.8 Hz, 1 H), 10.82 (s, 1H), 11.79 (s, 1H), 11.89 (s, 1H). Anal. Calc. for $C_{11}H_{13}N_4O_2I$: C, 36.69; H 3.64; N, 15.56; I, 35.24. Found: C, 36.91; H, 3.58; N, 15.65; I, 35.56.

In a similar fashion from 2,3-diiodo-4-hydroxy-6-methylpyrrolo[2,3-d]pyrimidine and 2,3-diiodo-4-hydroxypyrrolo[2,3-d]pyrimidine, there are respectively obtained 3-iodo-4-hydroxy-6-methylpyrrolo[2,3-d]pyrimidine and 3-iodo-4-hydroxypyrrolo[2,3-d]pyrimidine, mp >245° C. (compound loses iodine). $^1$NMR (d$_6$-DMSO) δ7.20 (d, J=2.2 Hz, 1H), 7.82 (d, J=2.8 Hz, 1H), 11.85 (d, J=1.1 Hz, 1H), 12.17 (s, 1H).

EXAMPLE 2

Dimethyl N-[4-(4-Hydroxy-6-pivaloylaminopyrrolo-[2,3-d]pyrimidin-3-ylethynyl)benzoyl]-L-glutamate To a mixture of 3.6 g (10 mmol) of well-dried 3-iodo-4-hydroxy-6-pivaloylaminopyrrolo[2,3-d]pyrimidine in 40 mL of dimethylformamide are added 4.0 g (13.19 mmol) of dimethyl N-(4-ethynylbenzoyl)-L-glutamate, 0.38 g of copper (I) iodide, 3 mL of triethylamine, and 1.0 g of tetrakis-(triphenylphosphine)palladium. This mixture is stirred at ambient temperatures for two hours and then poured into 500 mL of water. The solid is collected by filtration, air dried, and then refluxed in 200 mL of methanol. The mixture is cooled and the solid collected by filtration, dissolved in two liters of 10% methanol in methylene chloride, and chromatographed over silica. Initial black bands are rechromatographed and the combined colorless bands from the first and second runs are evaporated to give 3.5 g of dimethyl N-[4-(4-hydroxy-6-pivaloylaminopyrrolo[2,3-d]pyrimidin-3-ylethynyl)benzoyl]-L-glutamate which can be purified further by recrystallization from 50% methanol in methylene chloride.

mp 280°-285° C. $^1$NMR (d$_6$-DMSO) δ1.21 (s, 9H), 1.96-2.15 (m, 2H), 2.44 (t, J=7.5 Hz, 2H) 3.56 (s, 3H), 3.62 (s, 3H), 4.40-4.45 (m, 1H), 7.43 (s, 1H), 7.53 (d, J=8.4 Hz, 2 H), 7.87 (d, J=8.4 Hz, 2 H), 8.82 (d, J=7.4 Hz, 1 H), 10.95 (s, 1H), 11.95 (s, 1H).

Anal. Calc. for $C_{27}H_{29}N_{29}N_5O_7$: C, 60.56; H 5.46; N, 13.08. Found: C, 60.55; H, 5.46; N, 12.89.

In as similar fashion by substituting an equivalent amount of dimethyl N-(pent-4-ynoyl)-L-glutamate, dimethyl N-(hept-6-enoyl)-L-glutamate, and dimethyl N-(hex-5-ynoyl)-L-glutamate for dimethyl N-(4-ethynylbenzoyl)glutamate in the foregoing procedure, there are obtained dimethyl N-[5-(4-hydroxy-6-pivaloylaminopyrrolo[2,3-d]pyrimidin-3-yl)pent-4-ynoyl]-L-glutamate, dimethyl N-[7-(4-hydroxy-6-pivaloylaminopyrrolo[2,3-d]pyrimidin-3-yl)hept-6-enoyl]-L-glutamate, and dimethyl N-[6-(4-hydroxy-6-pivaloylaminopyrrolo[2,3-d]pyrimidin3-yl)hex-5-ynoyl]-L-glutamate.

Dimethyl N-(hex-5-ynoyl)-L-glutamate can be obtained in the manner described generally in U.S. Pat. No. 4,882,333, the disclosure of which is incorporated herein by reference, by allowing hex-5-ynoic acid chloride (obtained by treating hex-5-ynoic acid with thionyl chloride) to react with dimethyl L-glutamate in the presence of an acid acceptor such as triethylamine. Hex-5-ynoic acid in turn can be prepared, for example, by alkaline hydrolysis of 5-cyanopent-1-yne.

EXAMPLE 3

Diethyl N-[4- {1-Hydroxy-3-(4-hydroxy-6-amino-pyrrolo-[2,3-d]pyrimidin-3-yl)prop-2-yl}-benzoyl]-glutmate A mixture of 14.6 g of 3-iodo-4-hydroxy-6-pivaloylaminopyrrolo[2,3-d]pyrimidine, 7.6 g of 2-(2-propynyloxy)-tetrahydropyran, 798 mg (10%) of palladium chloride, 2.36 g (20%) of triphenyl phosphine, 428 mg (5%) of cuprous iodide, 45 ml of triethyl amine and 700 ml of acetonitrile is heated at reflux under nitrogen for 12 hours. There then are added to the hot reaction mixture 3.2 g of 2-(2-propynyloxy)-tetrahydropyran and reflux is continued for an additional 12 hours. After heating for a total of 24 hours under reflux, the solvent is removed under reduced pressure, and the residue filtered through silica gel using 2% methanol in methylene chloride. This filtrate is concentrated and chromatographed on silica gel eluting with 20:1 ethyl acetate:hexane mixture to give 3-(3-tetrahydropyr-2-yloxy-prop-1-yn-1-yl)-4-hydroxy-6-pivaloylaminopyrrolo[2,3-d]pyrimidine which is further purified by recrystallization with ethyl acetate.

A mixture of 2 g of 3-(3-tetrahydropyr-2-yloxyprop-1-yn-1-yl)-4-hydroxy-6-pivaloylaminopyrrolo[2,3-d]pyrimidine, 40 ml of methanol, 20 ml of chloroform, 40 mg of 5% palladium on barium sulfate, and 40 mg of synthetic quinoline is stirred under 1 atmosphere hydrogen pressure for 40 min. The solvent then is removed by evaporation and the residue diluted with methylene chloride. The methylene chloride solution is filtered through silica gel with 2% methanol in methylene chloride to remove catalyst and the filtrate then concentrated to give an oil which upon adding ether yields 3-(3-tetrahydropyr-2-yloxyprop-1-en-1-yl)-4-hydroxy-6-pivaloylaminopyrrolo[2,3-d]pyrimidine which can be further purified through column chromatography eluting with ethyl acetate and recrystallization using ethyl acetate.

A mixture containing 3.48 g of 3-(3-tetrahydropyr-2-yloxyprop-1-en-1-yl)-4-hydroxy-6-pivaloylaminopyrrolo[2,3-d]pyrimidine, 3.12g (1.2 equiv.) of diethyl N-(4-iodobenzoyl)glutamate, 546 mg (20%) of tris-(2-methylphenyl)phosphine, 201 mg (10%) of palladium acetate and 85.5 mg (5%) of cuprous iodide in 15 ml of triethylamine and 240 ml of acetonitrile is heated at reflux under nitrogen. After 12 hours., 1.17 g of ethyl N-(4-iodobenzoyl)glutamate are added and the reaction mixture is heated at reflux under nitrogen for an additional 12 hours. The reaction mixture then is concentrated under reduced pressure and the residue chromatographed on silica gel, eluting with 20:1 ethyl acetate:-hexane. (Any recovered starting material can be recycled through the foregoing procedure.) The concentrated material is dissolved in 1:5 ethyl acetate:ether and this solution is refrigerated for 15 hours. The solid which forms is collected by filtration, washed with cold ethyl acetate and dried to yield diethyl N-[4-{1-(tetrahydropyr-2-yloxy)-3-(4-hydroxy-6-pivaloylaminopyrrolo[2,3-d]pyrimidin-3-yl)prop-2-en-2yl}benzoyl]glutamate.

EXAMPLE 4

Dimethyl N-[5-(4-Hydroxy-6-pivaloylamino-pyrrolo[2,3-d]pyrimidin-3-yl}ethynyl)-thien-2-ylcarbonyl]-L-glutamate A mixture of 2.0 g of 3-iodo-4-hydroxy-6-pivaloylaminopyrrolo[2,3-d]pyrimidine, 1.2 g. of trimethylsilylacetylene, 0.1 g of palladium chloride, 0.23 g of triphenylphosphine, 0.06 g of cuprous iodide, and 2.6 g of triethylamine in 100 mL of acetonitrile is heated in a sealed tube for 1.5 hours at 50° C. and then at reflux for 3 hours. The solvent is removed under reduced pressure and the residue triturated with 1:1 ethyl acetate:hexanes and filtered. The solid thus collected is dissolved in methylene chloride and this solution is passed through a pad of silica gel eluting with 1% methanol on methylene chloride. The eluate is concentrated to yield 3-trimethylsilylethynyl-4-hydroxy-6-pivaloylaminopyrrolo[2,3-d]pyrimidine.

To a solution of 1.5 g of 3-trimethylsilylethynyl--4-hydroxy-6-pivaloylaminopyrrolo[2,3-d]pyrimidine in 100 mL of anhydrous tetrahydrofuran cooled to 0° C. are added under nitrogen 4.75 mL of 1M tetrabutylammonium fluoride in anhydrous tetrahydrofuran. After 5 minutes, the reaction mixture is allowed to attain room temperature and is then stirred for 2 hours. The solvent is removed under reduced pressure and the residue purified by chromatography over silica gel to yield 3-ethynyl-4-hydroxy-6-pivaloylaminopyrrolo[2,3-d]pyrimidine.

A mixture of 1.70 g. of 3-ethynyl-4-hydroxy-6-pivaloylaminopyrrolo[2,3-d]pyrimidine, 2.30 g. of dimethyl N-(5-bromothien-2-ylcarbonyl)-L-glutamate (prepared as described in U.S. Pat. No. 4,882,334, the disclosure of which is incorporated herein by reference), 44 mg. of palladium chloride, 130 mg. of triphenylphosphine, 25 mg. of cuprous iodide, and 1.13 mL. of triethylamine in 30 mL. of acetonitrile is heated at reflux for 3 hours and then cooled to ambient temperature. The solvent is removed under reduced pressure and the residue column chromatographed (Waters 500) eluting with 1:19 methanol:methylene chloride to yield dimethyl N-[5-(4-hydroxy-6-pivaloylaminopyrrolo[2,3-d]pyrimidin-3-yl}ethynyl)thien-2-ylcarbonyl]-L-glutamate.

By substituting equivalent amounts of diethyl N(-4-bromothien-2-ylcarbony)-L-glutamate, and diethyl N(-5-bromothien-3-ylcarbony)-L-glutamate in the foregoing procedure, there are respectively obtained diethyl N-[4-(4-hydroxy-6-pivaloylaminopyrrolo[2,3-d]pyrimidin-3-ylethynyl)thien-2-ylcarbonyl]-L-glutamate and diethyl N-[5-(4-hydroxy-6-pivaloylaminopyrrolo[2,3-d]pyrimidin-3-ylethynyl)thien-3-ylcarbonyl]-L-glutamate.

Similarly from dimethyl N-(2-fluoro-4-iodobenzoyl)-L-glutamate and dimethyl N-(3-fluoro-4-iodobenzoyl)-L-glutamate (prepared as described in Ser. No. 156,908 filed Feb. 5, 1988, the disclosure of which is incorporated herein by reference), there are respectively obtained dimethyl N-[2-fluoro-4-(4-hydroxy-6-pivaloylaminopyrrolo[2,3-d]pyrimidin-3-ylethynyl)benzoyl]-L-glutamate and dimethyl N-[3-fluoro-4-(4-hydroxy-6-pivaloylaminopyrrolo[2,3-d]pyrimidin-3-ylethynyl)benzoyl]-L-glutamate.

EXAMPLE 5

Dimethyl N-[4-(4-Hydroxyprrolo[2,3-d]pyrimidin-3-ylethynyyl)-benzoyl]-L-glutamate By allowing each of 3-iodo-4-hydroxy-6-methylpyrrolo[2,3-d]pyrimidine and 3-iodo-4-hydroxypyrrolo[2,3-d]pyrimidine to react with dimethyl N-(4-ethynylbenzoyl)-L-glutamate in the manner described in Example 2, there are respectively obtained dimethyl N-4-(4-hydroxy-6-methylpyrrolo[2,3-d]pyrimidin-3-ylethynyl)benzoyl]-L-glutamate and dimethyl N-[4-(4-hydroxypyrrolo[2,3-d]pyrimidin-3-ylethynyl)benzoyl]-L-glutamate. The latter compound upon purification by chromatography over silica gives the following physical properties: mp 160° C. (dec.).

$^1$NMR (d$_6$-DMSO) δ1.98–2.15 (m, 2H), 2.45 (t, J=7.5 Hz, 2H) 3.57 (s, 3H), 3.64 (s, 3H), 4.40–4.45 (m, 1H), 7.51 ((d, J=2.5 Hz, 1H), 7.55 (d, J=8.2 Hz, 2 H), 7.87 (s, 1H), 7.90 (d, J=8.2 Hz, 1 H), 11.97 ((d, J=3.7 Hz, 1 H), 12.31 (s, 1H).

Alternatively, by substituting equivalent amounts of methyl 4-ethynylbenzoate, 4-ethynyltoluene, 4-ethynylbenzene, 1-chloro-4-ethynylbenzene, 1-fluoro-4-ethynylbenzene, and 1-methoxy-4-ethynylbenzene in the procedure of Example 2, there are obtained methyl 4-(4-hydroxy-6-pivaloylaminopyrrolo[2,3-d]pyrimidin-3-ylethynyl)benzoate, 3-(4-methylphenyl)ethynyl-4-hydroxy-6-pivaloylaminopyrrolo[2,3-d]pyrimidine, 3-phenylethynyl-4-hydroxy-6-pivaloylaminopyrrolo[2,3-d]pyrimidine, 3-(4-chlorophenyl)ethynyl-4-hydroxy-6-pivaloylaminopyrrolo[2,3-d]pyrimidine, 3-(4-fluorophenyl)ethynyl-4-hydroxy-6-pivaloylaminopyrrolo[2,3-d]pyrimidine, and 3-(4-methoxyphenyl)ethynyl-4-hydroxy-6-pivaloylaminopyrrolo[2,3-d]pyrimidine.

Use of 3-iodo-4-hydroxy-6-methylpyrrolo[2,3-d]pyrimidine in place of 3-iodo-4-hydroxy-6-pivaloylaminopyrrolo[2,3-d]pyrimidine with the foregoing iodo compounds yields methyl 4-(4-hydroxy-6-methylpyrrolo-[2,3-d]pyrimidin-3-ylethynyl)benzoate, 3-(4-methylphenyl)ethynyl-4-hydroxy-6-methylpyrrolo[2,3-d]pyrimidine,3-phenylethynyl-4-hydroxy-6-methylpyrrolo-[2,3-d]pyrimidine, 3-(4-chlorophenyl)ethynyl-4-hydroxy-6-methylpyrrolo-[2,3-d]pyrimidine, 3-(4-fluorophenyl)ethynyl-4-hydroxy-6-methylpyrrolo[2,3-d]pyrimidine, and 3-(4-methoxyphenyl)ethynyl-4-hydroxy-6-methylpyrrolo[2,3-d]pyrimidine.

Use of 3-iodo-4-hydroxypyrrolo[2,3-d]pyrimidine in place of 3-iodo-4-hydroxy-6-pivaloylaminopyrrolo[2,3-d]pyrimidine with the foregoing iodo compounds yields respectively methyl 4-(4-hydroxypyrrolo[2,3-d]pyrimidin-3-ylethynyl)benzoate, 3-(4-methylphenyl)ethynyl-4-hydroxypyrrolo[2,3-d]pyrimidine, 3-phenylethynyl-4-hydroxypyrrolo[2,3-d]pyrimidine, 3-(4 -chlorophenyl)ethynyl-4-hydroxypyrrolo[2,3-d]pyrimidine, 3-(4-fluoro- phenyl)ethynyl-4-hydroxypyrrolo[2,3-d]pyrimidine, and 3-(4-methoxyphenyl)ethynyl-4-hydroxypyrrolo[2,3-d]pyrimidine.

EXAMPLE 6

Dimethyl N-{4-[2-(4-Hydroxy-6-pivaloylaminopyrrolo-[2,3-d]pyrimidin-3-yl)ethyl]benzoyl}-L-glutamate A mixture of 1.0 g of dimethyl N-[4-(4-hydroxy-6-pivaloylaminopyrrolo[2,3-d]pyrimidin-3-ylethynyl)benzoyl]-L-glutamate in 250 mL of 50% methanol in methylene chloride and 0.8 g of 3% palladium-on-carbon is hydrogenated at 50 p.s.i. for three hours, filtered, and concentrated under reduced pressure. The solid is collected by filtration and dried to yield 0.72 g of dimethyl N-{4-[2-(4-hydroxy-6-pivaloylaminopyrrolo[2,3d-]pyrimidin-3-yl)ethyl]benzoyl}-L-glutamate. mp 247°0 C.

$^1$NMR (d$_6$-DMSO) δ1.21 (s, 9H), 1.90–2.12 (m, 2H), 2.42 (t, J=7.4 Hz, 2H), 2.92 (t, J=4 Hz, 2H), 2.97 (t, J=4 Hz, 2H), 3.55 (s, 3H), 3.61 (s, 3H), 4.38–4.45 (m, 1H), 6.61 (s, 1H), 7.27 (d, J=8.2 Hz, 2 H), 7.75 (d, J=8.2 Hz, 2 H), 8.64 (d, J=7.4 Hz, 1 H), 10.75 (s, 1H), 11.22 (s, 1H).

Anal. Calc. for $C_{27}H_{33}N_5O_7$: C, 60.10; H 6.17; N, 12.98. Found: C, 59.94; H, 6.15; N, 12.72.

EXAMPLE 7

Dimethyl N-{5-[2-(4-Hydroxy-6-pivaloylaminopyrrolo-2,3-d]pyrimidin-3-yl)ethyl]thien-2-ylcarbonyl}-L-glutamate By subjecting dimethyl N-[5-(4-hydroxy-6-pivaloylaminopyrrolo[2,3-d]pyrimidin-3-yl}ethynyl)-thien-2-ylcarbonyl]-L-glutamate to the hydrogenation procedure of Example 6, there is obtained dimethyl N-{5-[2-(4 -hydroxy-6-pivaloylaminopyrrolo[2,3-d]pyrimidin-3-yl)ethyl]thien-2-ylcarbonyl}-L-glutamate.

Similarly the following compounds are subjected to the hydrogenation of Example 6:

(a) dimethyl N-[2-fluoro-4-(4-hydroxy-6-pivaloylaminopyrrolo[2,3-d]pyrimidin-3-ylethynyl)-benzoyl]-L-glutamate;
(b) dimethyl N-[3-fluoro-4-(4-hydroxy-6-pivaloylaminopyrrolo[2,3-d]pyrimidin-3-ylethynyl)-benzoyl]-L-glutamate;
(c) diethyl N-[4-(4-hydroxy-6-pivaloylaminopyrrolo[2,3-d]pyrimidin-3-ylethynyl)thien-2-ylcarbonyl]-L-glutamate;
(d) diethyl N-[5-(4-hydroxy-6-pivaloylaminopyrrolo[2,3-d]pyrimidin-3-ylethynyl)thien-3-ylcarbonyl]-L-glutamate;
(e) dimethyl N-[5-(4-hydroxy-6-pivaloylaminopyrrolo[2,3-d]pyrimidin-3-yl)pent-4-ynoyl]-L-glutamate;
(f) dimethyl N-[7-(4-hydroxy-6-pivaloylaminopyrrolo[2,3-d]pyrimidin-3-yl)hept-6-enoyl]-L-glutamate;
(g) dimethyl N-[6-(4-hydroxy-6-pivaloylaminopyrrolo[2,3-d]pyrimidin-3-yl)hex-5-ynoyl]-L-glutamate;
(h) methyl 4-(4-hydroxy-6-pivaloylaminopyrrolo[2,3-d]pyrimidin-3-ylethynyl)benzoate;
(i) 3-(4-methylphenyl)ethynyl-4-hydroxy-6-pivaloylaminopyrrolo[2,3-d]pyrimidine;
(j) 3-phenylethynyl-4-hydroxy-6-pivaloylaminopyrrolo[2,3-d]pyrimidine;
(k) 3-(4-chlorophenyl)ethynyl-4-hydroxy-6-pivaloylaminopyrrolo[2,3-d]pyrimidine;
(l) 3-(4-fluorophenyl)ethynyl-4-hydroxy-6-pivaloylaminopyrrolo[2,3-d]pyrimidine;
(m) 3-(4-methoxyphenyl)ethynyl-4-hydroxy-6-pivaloylaminopyrrolo[2,3-d]pyrimidine;
(n) methyl 4-(4-hydroxy-6-methylpyrrolo[2,3-d]pyrimidin-3-ylethynyl)benzoate;
(o) 3-(4-methylphenyl)ethynyl-4-hydroxy-6-methylpyrrolo[2,3-d]pyrimidine;
(p) 3-phenylethynyl-4-hydroxy-6-methylpyrrolo[2,3d-]pyrimidine;
(q) 3-(4-chlorophenyl)ethynyl-4-hydroxy-6-methylpyrrolo[2,3-d]pyrimidine;

(r) 3-(4-fluorophenyl)ethynyl-4-hydroxy-6-methylpyrrolo[2,3-d]pyrimidine;
(s) 3-(4-methoxyphenyl)ethynyl-4-hydroxy-6-methylpyrrolo[2,3-d]pyrimidine;
(t) methyl 4-(4-hydroxypyrrolo[2,3-d]pyrimidin-3-ylethynyl)benzoate;
(u) 3-(4-methylphenyl)ethynyl-4-hydroxypyrrolo[2,3-d]pyrimidine;
(v) 3-phenylethynyl-4-hydroxypyrrolo[2,3-d]pyrimidine;
(w) 3-(4-chlorophenyl)ethynyl-4-hydroxypyrrolo[2,3-d]pyrimidine;
(x) 3-(4-fluorophenyl)ethynyl-4-hydroxypyrrolo[2,3-d]pyrimidine; and
(y) 3-(4-methoxyphenyl)ethynyl-4-hydroxypyrrolo[2,3-d]pyrimidine.

There are respectively obtained:
(a) dimethyl N-[2-fluoro-4-(4-hydroxy-6-pivaloylaminopyrrolo[2,3-d]pyrimidin-3-ylethyl)benzoyl]-L-glutamate;
(b) dimethyl N-[3-fluoro-4-(4-hydroxy-6-pivaloylaminopyrrolo[2,3-d]pyrimidin-3-ylethyl)benzoyl]-L-glutamate;
(c) diethyl N-[4-(4-hydroxy-6-pivaloylaminopyrrolo[2,3-d]pyrimidin-3-ylethyl)thien-2-ylcarbonyl]-L-glutamate;
(d) diethyl N-[5-(4-hydroxy-6-pivaloylaminopyrrolo[2,3-d]pyrimidin-3-ylethyl)thien-3-ylcarbonyl]-L-glutamate;
(e) dimethyl N-[5-(4-hydroxy-6-pivaloylaminopyrrolo[2,3-d]pyrimidin-3-yl)pentyl]-L-glutamate;
(f) dimethyl N-[7-(4-hydroxy-6-pivaloylaminopyrrolo[2,3-d]pyrimidin-3-yl)heptyl]-L-glutamate;
(g) dimethyl N-[6-(4-hydroxy-6-pivaloylaminopyrrolo[2,3-d]pyrimidin-3-yl)hexyl]-L-glutamate;
(h) methyl 4-[2-(4-hydroxy-6-pivaloylaminopyrrolo[2,3-d]pyrimidin-3-yl)ethyl]benzoate;
(i) 3-[2-(4-methylphenyl)ethyl]-4-hydroxy-6-pivaloylaminopyrrolo[2,3-d]pyrimidine;
(j) 3-(2-phenylethyl)-4-hydroxy-6-pivaloylaminopyrrolo[2,3-d]pyrimidine;
(k) 3-[2-(4-chlorophenyl)ethyl]-4-hydroxy-6-pivaloylaminopyrrolo[2,3-d]pyrimidine;
(l) 3-[2-(4-fluorophenyl)ethyl]-4-hydroxy-6-pivaloylaminopyrrolo[2,3-d]pyrimidine;
(m) 3-[2-(4-methoxyphenyl)ethyl]-4-hydroxy-6-pivaloylaminopyrrolo[2,3-d]pyrimidine;
(n) methyl 4-[2-(4-hydroxy-6-methylpyrrolo[2,3-d]pyrimidin-3-yl)ethyl]benzoate;
(o) 3-[2-(4-methylphenyl)ethyl]-4-hydroxy-6-methylpyrrolo[2,3-d]pyrimidine;
(p) 3-(2-phenylethyl)-4-hydroxy-6-methylpyrrolo[2,3-d]pyrimidine;
(q) 3-[2-(4-chlorophenyl)ethyl]-4-hydroxy-6-methylpyrrolo[2,3-d]pyrimidine;
(r) 3-[2-(4-fluorophenyl)ethyl]-4-hydroxy-6-methylpyrrolo[2,3-d]pyrimidine;
(s) 3-[2-(4-methoxyphenyl)ethyl]-4-hydroxy-6-methylpyrrolo[2,3-d]pyrimidine;
(t) methyl 4-[2-(4-hydroxypyrrolo[2,3-d]pyrimidin3-yl)ethyl]benzoate;
(u) 3-[2-(4-methylphenyl)ethyl]-4-hydroxypyrrolo[2,3-d]pyrimidine;
(v) 3-(2-phenylethyl)-4-hydroxypyrrolo[2,3-d]pyrimidine;
(w) 3-[2-(4-chlorophenyl)ethyl]-4-hydroxypyrrolo[2,3-d]pyrimidine;
(x) 3-[2-(4-fluorophenyl)ethyl]-4-hydroxypyrrolo[2,3-d]pyrimidine; and
(y) 3-[2-(4-methoxyphenyl)ethyl]-4-hydroxypyrrolo[2,3-d]pyrimidine.

EXAMPLE 8

Diethyl N-[4-{1-(Tetrahydropyr-2-yloxy)-3-(4-hydroxy-6-pivaloylaminpyrrolo[2,3-d]pyrimidin-3-yl)prop-2yl}benzoyl]glutamate A solution of 1.16 g of diethyl N-[4-{1-(tetrahydropyr-2-yloxy)-3-(4-hydroxy-6-pivaloylaminopyrrolo[2,3-d]pyrimidin-3-yl)prop-2-en-2-yl}benzoyl]-glutamate and 174 mg (20%) of amorphous platinum (IV) oxide in 150 ml of glacial acetic acid is hydrogenated for 10 hours at 50 psi. The reaction mixture is diluted with 50 ml of methanol and filtered through Celite. The filtrate is concentrated and diluted with ethyl acetate. The solid which forms after cooling for 15 hour is collected by filtration, washed with cold ethyl acetate and dried to give diethyl N-[4-{1-(tetrahydropyr-2-yloxy)-3-(4-hydroxy-6-pivaloylaminopyrrolo[2,3-d]pyrimidin-3-yl)prop--2-yl}benzoyl]glutamate.

EXAMPLE 9

Dimethyl N-{4-[2-(4-Hydroxypyrrolo[2,3-d]pyrimidin-3-yl)ethyl]benzoyl}-L-glutamate A mixture of 1.1 g of dimethyl N-[4-(4-hydroxypyrrolo[2,3-d]pyrimidin-3-ylethynyl)benzoyl]-L-glutamate in 100 mL of 50% methanol in methylene chloride and 0.8 g of 3% palladium-on-carbon is hydrogenated at 50 p.s.i. for 24 hours, filtered, and concentrated under reduced pressure. Ether is added to the residue and the solid is collected by filtration and dried to yield 0.67 g of dimethyl N-{4-[2-(4-hydroxyaminopyrrolo[2,3-d]pyrimidin-3-yl)ethyl]benzoyl}-L-glutamate. mp 170°–172° C.

$^1$NMR (d$_6$-DMSO) δ1.94–2.14 (m, 2H), 2.44 (t, J=7.4 Hz, 2H), 2.93–3.02 (m, 2H), 3.57 (s, 3H), 3.63 (s, 3H), 4.40–4.70 (m, 1H), 6.71 (s, 1H), 7.29 (d, J=8.2 Hz, 2 H), 7.77 (m, 3 H), 8.66 (d, J=7.4 Hz, 1 H), 11.52 (s, 1H), 11.71 (s, 1H).

In a similar fashion from dimethyl N-[4-(4-hydroxy-6-methylpyrrolo[2,3-d]pyrimidin-3-ylethynyl)benzoyl]-L-glutamate, there is obtained according to this procedure dimethyl N-(4-[2-(4-hydroxyamino-6-methylpyrrolo[2,3-d]pyrimidin-3-yl)ethyl]benzoyl}-L-glutamate.

EXAMPLE 10

N-{4[2-(4-Hydroxy-6-pivaloyaminopyrrolo[2,3-d]-pyrimidin-3-ethyl]benzoyl)-L-glutamic acid A mixture of 1.5 g of dimethyl N-{4-[2-(4-hydroxy-6-pivaloylaminopyrrolo[2,3-d]pyrimidin-3-yl)ethyl]benzoyl}-L-glutamate in 10 mL of 1N sodium hydroxide is stirred at ambient temperatures for three days to form the sodium salt of N-{4-[2-(4-hydroxy-6-aminopyrrolo2,3-d]pyrimidin-3-yl)ethyl]benzoyl}-L-glutamic acid. This is neutralized with glacial acetic acid. The solid which forms is collected by filtration and recrystallized from 50% methanol in methylene chloride to give 0.8 g (67%) of N-(4-[2-(4-hydroxy-6-aminopyrrolo[2,3-d]pyrimidin-3-yl)ethyl]benzoyl}-L-glutamic acid.

$^1$NMR (d$_6$-DMSO) δ1.80–2.00 (m, 2H), 2.10–2.30 (m, 2H), 2.77–2.820 (m, 2H), 2.89–2.93 (m, 2H), 4.13–4.19

(m, 2H), 6.25 (d, J=1.3 Hz, 1H), 7.23 (d, J=8.1 Hz, 2 H), 7.69 (d, J=8.1 Hz, 2 H), 8.13 (d, J=6.7 Hz, 1 H), 10.55 (s, 1H)

EXAMPLE 11

Diethyl N-[4-{1-Hydroxy-3-(4-hydroxy-6-pivaloylaminopyrrolo[2,3-d]pyrimidin-3-yl)prop-2-yl}benzoyl]-glutamate The solution of 0.94 g of diethyl N-[4-55 1-(tetrahydropyr-2-yloxy)-3-(4-hydroxy-6-pivaloylaminopyrrolo[2,3-d]pyrimidin-3-yl)prop-2-yl}benzoyl]glutamate in 40 ml of 0.1N methanolic hydrogen chloride is stirred at ambient temperatures for 2 hours. The reaction mixture is neutralized with a solution of 205 mg of sodium carbonate in 10 ml of water and most of methanol removed by evaporation under reduced pressure. One hundred milliliters of methylene chloride are added and the solution is washed twice with 20 ml of water, dried over anhydrous magnesium sulfate, and concentrated. The residue is triturated with 1:2 ethyl acetate and ether, filtered, and dried to give diethyl N-[4-{1-hydroxy-3-(4-hydroxy-6-pivaloylamino-pyrrolo[2,3-d]pyrimidin-3-yl)prop-2-yl}benzoyl]glutamate.

EXAMPLE 12

N-[4-{(1-Hydroxy-3-(4-hydroxy 6-aminopyrrolo[2,3-d]}benzoyl]glutamic acid

A solution of 0.3 g of diethyl N-[4-(1-hydroxy--3(4-hydroxy-6-pivaloylaminopyrrolo[2,3d]-pyrimidin-3-yl)prop-2-yl}benzoyl]glutamate in 9 ml of 1N aqueous sodium hydroxide is stirred under nitrogen at ambient temperature for 72 hours. The reaction mixture is rendered slightly acidic (pH=~4) with 1N hydrochloric acid and filtered. The solid thus collected is washed with water (5 ml) and cold ethanol (5 ml) and dried to give N-[4-{1-hydroxy-3-(4-hydroxy-6-aminopyrrolo[2,3-d]-pyrimidin-3-yl)prop-2-yl}benzoyl]}-L-glutamic acid.

Similarly from dimethyl N-{(2-fluoro-4-[2-(4-hydroxy-6-pivaloylaminopyrrolo[2,3-d]pyrimidin-3-yl)ethyl]benzoyl}-L-glutamate and dimethyl N-(3-fluoro-4-[2-(4-hydroxy-6-pivaloylaminopyrrolo[2,3-d]pyrimidin-3yl)ethyl]benzoyl}-L-glutamate there are respectively obtained according to the foregoing procedure N-{2-fluoro-4-[2-(4-hydroxy-6-aminopyrrolo[2,3-d]pyrimidin-3yl)ethyl]benzoyl}-L-glutamic acid and N-{3-fluoro-4-[2(4-hydroxy-6-aminopyrrolo[2,3-d]pyrimidin-3-yl)ethyl]benzoyl}-L-glutamic acid.

In an analogous fashion to the foregoing procedure, there are respectively obtained from dimethyl N-{-5-[2-(4-hydroxy-6-pivaloylaminopyrrolo[2,3-d]pyrimidin-3-yl)ethyl]thien-2-ylcabonyl}-L-glutamate, diethyl N-{4-[2-(4-hydroxy-6-pivaloylaminopyrrolo[2,3-d]pyrimidin-3-yl)ethyl]thien-2-ylcabonyl}-L-glutamate, and diethyl N-{5-[2-(4-hydroxy-6-pivaloylaminopyrrolo[2,3d-]pyrimidin-3-yl)ethyl]thien-3-ylcabonyl}-L-glutamate, the compounds N-{5-[2-(4-hydroxy-6-aminopyrrolo[2,3-d]pyrimidin-3-yl)ethyl]thien-2-ylcarbonyl}-L-glutamic acid, N-[4-[2-(4-hydroxy-6-aminopyrrolo[2,3-d]pyrimidin-3-yl)ethyl]thien-2-ylcarbonyl}-L-glutamic acid, and N-{5-[2-(4-hydroxy-6-aminopyrrolo[2,3-d]pyrimidin-3yl)ethyl]thien-3-ylcarbonyl}-L-glutamic acid.

Similarly obtained from dimethyl N-[5-(4-hydroxy6-pivaloylaminopyrrolo[2,3-d]pyrimid-in--3-yl)pentanoyl]-L-glutamate, dimethyl N-[7-(4-hydroxy-6-pivaloylaminopyrrolo[2,3-d]pyrimidin-3-yl)heptanoyl]-L-glutamate, and dimethyl N-[6-(4-hydroxy-6-pivaloylaminopyrrolo[2,3-d]pyrimidin-3-yl)-hexanoyl]-L-glutamate, are, respectively, N-[5-(4-hydroxy-6-aminopyrrolo[2,3-d]-pyrimidin-3-yl)pentanoyl]-L-glutamic acid, N-[7-(4-hydroxy-6-aminopyrrolo[2,3-d]pyrimidin-3-yl)heptanoyl]-L-glutamic acid, and N-[6-(4-hydroxy-6-aminopyrrolo[2,3d]pyrimidin-3-yl)hexanoyl]-L-glutamic acid.

EXAMPLE 13

N-{4-[2-(4-Hydroxpyrrolo[2,3-d]pyrimidin-3-yl)ethyl]-benzoyl}-L-glutamic acid

A mixture of 0.5 g of dimethyl N-{4-[2-(4hydroxypyrrolo[2,3-d]pyrimidin-3-yl)ethyl]benzoyl}-L-glutamate in 3 mL of 1N sodium hydroxide is stirred at ambient temperatures for three days to form the sodium salt of N-{4-[2-(4-hydroxy-6-aminopyrrolo[2,3-d]pyrimidin-3-yl)ethyl]benzoyl}-L-glutamic acid. This is neutralized with hydrochloric acid. The solid which forms is collected by filtration and recrystallized from methanol by addition of water to give 0.35 g (75%) of N-{4-[2-(4-hydroxypyrrolo[2,3-d]pyrimidin-3-yl)ethyl]benzoyl}-L-glutamic acid.

$^1$NMR (d$_6$-DMSO) δ1.88–2.12 (m, 2H), 2.33 (t, J=7.3 Hz, 2H), 2.97 (m, 4H), 4.33–4.40 (m, 1H), 6.70 (d, J=1.2 Hz,1H), 7.28 (d, J=7.0 Hz, 2 H), 7.76 (m, 3H), 8.50 (d, J=7.6 Hz, 1H), 11.48 (s, 1H), 11.67 (s, 1H), 12.40 (br, 1H).

In a similar fashion from dimethyl N-{4-[2-(4-hydroxy-6-methylpyrrolo[2,3-d]pyrimidin-3-yl)ethyl]-benzoyl}-L-glutamate, there is obtained according to the foregoing procedure first the sodium salt of N-{4-[2-(4-hydroxy-6-methylpyrrolo[2,3-d]pyrimidin-3-yl)ethyl]benzoyl}-L-glutamic acid which upon neutralization with glacial acetic acid yields N-{4-[2,3-d]pyrimidine; 2-(4-hydroxy-6-methylpyrrolo[2,3-d]pyrimidin-3-yl)ethyl]benzoyl}-L-glutamic acid.

By subjecting methyl 4-[2-(4-hydroxy-6-pivaloylaminopyrrolo[2,3-d]pyrimidin-3-yl)ethyl]benzoate; 3-[2-(4-methylphenyl)ethyl]-4-hydroxy-6-pivaloylaminopyrrolo[2,3-d]pyrimidine; 3-(2-phenylethyl)-4-hydroxy-6-pivaloylaminopyrrolo[2,3-d]pyrimidine; 3-[2-(4-chlorophenyl)ethyl]-4-hydroxy-6-pivaloylaminopyrrolo[2,3-d]pyrimidine; 3-[2-(4-fluorophenyl)ethyl]-4-hydroxy-6-pivaloylaminopyrrolo[2,3-d]pyrimidine; 3-[2-(4-methoxyphenyl)ethyl]-4-hydroxy-6-pivaloylaminopyrrolo[2,3-d]pyrimidine; and methyl 4-[2-(4-hydroxy-6-methylpyrrolo[2,3-d]pyrimidin-3-yl)ethyl]benzoate to the foregoing procedure, there are respectively obtained 4-[2-(4-hydroxy-6-aminopyrrolo[2,3-d]pyrimidin-3-yl)ethyl]benzoic acid; 3-[2-(4-methylphenyl)ethyl]-4-hydroxy-6-aminopyrrolo[2,3-d]pyrimidine; 3-(2-phenylethyl)-4-hydroxy-6-aminopyrrolo[2,3-d]pyrimidine; 3-[2- (4-chlorophenyl)ethyl]-4-hydroxy-6-aminopyrrolo[2,3-d] pyrimidine; 3-[2-(4-fluorophenyl)ethyl]-4-hydroxy-6aminopyrrolo[2,3-d]pyrimidine; 3-[2-(4-methoxyphenyl)ethyl]-4-hydroxy-6-aminopyrrolo[2,3-d]pyrimidine; and 4-[2-(4-hydroxy-6-methylpyrrolo[2,3-d]pyrimidin-3-yl)ethyl]benzoic acid.

What is claimed is:

1. A compound of the formula:

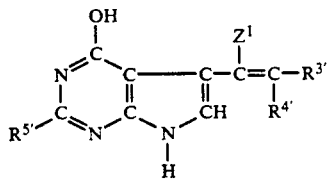

in which:

$R^{3'}$ is hydrogen, trimethylsilyl silyl group, or —$R^3$—$R^7$;

$R^3$ is phenylene, thienediyl, furanediyl, cyclohexanediyl, or alkanediyl of 2 to 4 carbon atoms;

$R^7$ is —COOR$^{2'}$, —CONHCH(COOR$_{2'}$)CH$_2$CH$_2$COOR$^{2'}$ $R^{2'}$ is hydrogen or carboxy protecting group;

$R_{4'}$, when taken independently of $Z^1$, is hydrogen, methyl, hydroxymethyl, or hydroxymethyl substituted with a hydroxy protecting group;

$R^{5'}$ is hydrogen, methyl, amino, or amino carrying a protecting group; and $Z^1$ is hydrogen, or $Z^1$ taken together with $R^{4'}$ is a carbon-carbon bond.

2. A compound of the formula:

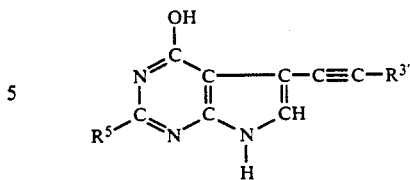

in which:
 $R_{3'}$ is hydrogen, trimethylsilyl silyl group, or —phenylene-$R^7$;
 $R^5$ is amino, or protected amino;
 $R^7$ is —COOOR$^{2'}$, —CONHCH(COOR$^{2'}$)CH$_2$CH$_2$COOR$^{2'}$); and
 $R^{2'}$ is hydrogen or carboxy protecting group.

3. A compound according to claim 2 wherein $R^{3'}$ is hydrogen of trimethylsilyl silyl group.

4. A compound according to claim 1 which is a 6-lower alkanamide of 3-ethynyl-4-hydroxy-6-aminopyrrolo[2,3d]pyrimidine.

5. A compound according to claim 1 which is 3-ethynyl-4hydroxy-6-pivaloylaminopyrrolo[2,3-d]pyrimidine.

6. A compound according to claim 1 which is 3-trimethylsilylethynyl-4-hydroxy-6-pivaloylaminopyrrolo[2,3-d]pyimidine.

7. A compound according to claim 1 which is dimethyl N-(4-(4-hydroxy-6-pivaloylaminopyrrolo-[2,3-d]pyrimidin-3-ylethynyl)benzoyl]-L-glutamate.

8. A compound according to claim 1 which is dimethyl N-[4-(4-hydroxypyrrolo[2,3-d]pyrimidin-3-ylethynl)benzoyl]-L-glutamate.

* * * * *